United States Patent [19]

Sun et al.

[11] Patent Number: 5,753,302
[45] Date of Patent: May 19, 1998

[54] ACOUSTIC DISPENSER

[75] Inventors: Hoi Cheong Steve Sun, Middlesex; Pabitra Datta, Mercer, both of N.J.; William Yat Chung Chiang, Newtown, Pa.; Howard Christopher Rivenburg, Mercer, N.J.; Bawa Singh, Camden, N.J.; Dominic S. Rosati; James Regis Matey, both of Mercer, N.J.

[73] Assignee: David Sarnoff Research Center, Inc., Princeton, N.J.

[21] Appl. No.: 661,211

[22] Filed: Jun. 10, 1996

Related U.S. Application Data

[63] Continuation-in-part of Ser. No. 630,049, Apr. 9, 1996.
[51] Int. Cl.⁶ .............. B05D 1/06; B05D 1/12; B05B 7/00; B05C 3/05
[52] U.S. Cl. ............ 427/180; 427/185; 427/201; 427/459; 427/483; 427/565; 427/600; 118/308; 118/311; 118/600; 118/612
[58] Field of Search ............ 118/600, 612, 118/57, 308, 311; 427/299, 346, 355, 560, 565, 600, 180, 201, 185, 483, 459, 460, 461; 222/196, 199; 73/570.5

[56] References Cited

U.S. PATENT DOCUMENTS

| | | | |
|---|---|---|---|
| 4,160,257 | 7/1979 | Carrish | 346/159 |
| 4,779,564 | 10/1988 | Kiefer et al. | 118/624 |
| 4,872,148 | 10/1989 | Kirby et al. | 367/172 |
| 4,948,497 | 8/1990 | Ohkawa | 209/1 |
| 4,971,257 | 11/1990 | Birge | 239/708 |
| 5,102,690 | 4/1992 | Iyer et al. | 427/57 |
| 5,310,582 | 5/1994 | Vyakarnam et al. | 427/560 |
| 5,497,763 | 3/1996 | Lloyd et al. | 128/200.14 |

OTHER PUBLICATIONS

Donald A. Seanor, Triboelectrification of Polymers in K.C. Frisch and A. Patsis, Electrical Properties of Polymers (Technomic Publications, Westport, CT) pp. 37–58.

*Primary Examiner*—Shrive Beck
*Assistant Examiner*—Michael Barr
*Attorney, Agent, or Firm*—William J. Burke

[57] ABSTRACT

The present invention provides an acoustic dispenser for propelling objects toward a substrate, together with methods of use of the dispenser. The acoustic dispenser uses a source of acoustic vibration and a membrane for the application of acoustic vibration wherein the objects are propelled from the membrane to a substrate. The acoustic dispenser and the methods of the invention can be used with numerous types of objects. In some embodiments, the objects are particles in a dry powder, which can include, for example, a pharmaceutically active ingredient. In other embodiments, the objects are beads, which preferably have an average diameter of about 100 to about 300 microns. Additionally, the acoustic dispenser can be used with more than one type of object, for example, two types of objects such as beads and dry powder. In some instances, the acoustic dispenser further comprises a membrane for separating one type of object from the other based on size, whereby one type of object is separated from the other prior to deposition.

26 Claims, 6 Drawing Sheets

ACOUSTIC DISPENSER

RELATED CO-PENDING U.S. PATENT APPLICATIONS

This application is a continuation-in-part of the application Ser. No. 08/630,049 ("Acoustic Dispenser," filed Apr. 9, 1996), which is incorporated herein in its entirety. Related U.S. patent applications, "Inhaler Apparatus with an Electronic Means for Enhanced Release of Dry Powders," filed simultaneously herewith, "Inhaler Apparatus with Modified Surfaces for Enhanced Release of Dry Powders," filed simultaneously herewith, U.S. Ser. Nos. 08/630,050 ("Electrostatic Chucks," filed Apr. 9, 1996) and its continuation-in-part, filed simultaneously herewith, U.S. Ser. No. 08/630,012 ("Chucks and Methods for Positioning Multiple Objects on a Substrate," filed Apr. 9, 1996). U.S. Ser. No. 08/471,889 ("Methods and Apparatus for Electronically Depositing a Medicament Powder Upon Predefined Regions of a Substrate," filed Jun. 6, 1995, and continuation-in-part thereof filed Jun. 6, 1996), U.S. Ser. No. 08/467,647 ("Apparatus for Electrostatically Depositing and Retaining Materials Upon a Substrate," filed Jun. 6, 1995 now U.S. Pat. No. 5,669,973) and U.S. Ser. No. 08/506,703 ("Inhaler Apparatus Using a Tribo-Electric Charging Technique," filed Jul. 25, 1995 now U.S. Pat. No. 5,642,727) describe, inter alia, the electrostatic deposition of objects, such as particles of powder, on a substrate, such as an inhaler substrate. The foregoing patent applications are hereby incorporated herein by reference, in their entirety.

The present invention provides an acoustic dispenser for propelling objects toward a substrate, together with methods of use of the dispenser. The acoustic dispenser uses a source of acoustic vibration and a membrane for the application of acoustic vibration wherein the objects are propelled from the membrane to a substrate.

In several industries, including, for example, the pharmaceutical industry and the paint industry, the use of a powder is required. The powder is propelled onto a surface, such as when a pharmaceutical tablet is coated or, for example, when a substrate is spray painted.

Generally, dry powders are propelled onto a surface using air to generate a cloud of powder. This process, however, suffers from several drawbacks, including, for example, propelling the particles of the powder in a random manner, which can lead to losses.

The present invention provides for an acoustic dispenser which provides several advantages over the use of air, for example, to propel a powder for deposition. The advantages include, for instance, the movement of particles in a directed manner rather than in a random manner, and a decrease in the amount of powder lost. Additionally, for example, the acoustic dispenser provides the ability to use an enclosed environment to deposit particles, which can be particularly advantageous when the particles are harmful to humans. Furthermore, for example, the acoustic dispenser can itself be used to electrostatically charge (also known as tribocharge) the particles, which provides for greater efficiency and is advantageous over corona charging, which can alter the chemical nature of certain particles.

SUMMARY OF THE INVENTION

The disadvantages heretofore associated with the prior art are overcome by inventive technique and apparatus for propelling objects such as particles toward a substrate for deposition. The present invention provides advantages including cost-effectiveness, efficiency and the ability to use an enclosed environment to deposit particles.

In one aspect, the present invention provides an apparatus for depositing objects on a surface, comprising:
   (a) a source of acoustic vibration;
   (b) a membrane for the application of acoustic vibration; and
   (c) a vessel for holding the objects.

In another aspect, the present invention provides an apparatus for depositing on a surface objects having an average diameter greater than about ten microns. The apparatus comprises:
   (a) a source of acoustic vibration;
   (b) a membrane for the application of acoustic vibration, the membrane comprising a conductive layer having multiple holes smaller than the average diameter of the particles; and
   (c) a vessel for holding the objects. Preferably, the membrane further comprises a dielectric layer having two surfaces, one of the surfaces being adjacent to the conductive layer having multiple holes, and the second surface of the dielectric layer being adjacent to a second conductive layer.

The acoustic dispenser and the methods of the invention can be used with numerous types of objects. In certain embodiments, the objects have an average diameter less than about ten microns, and in other embodiments, the objects have an average diameter greater than about ten microns. In some embodiments, the objects are particles in a dry powder, which can include, for example, a pharmaceutically active ingredient. In other embodiments, the objects are beads, which preferably have an average diameter of about 100 to about 300 microns. Additionally, the acoustic dispenser can be used with more than one type of object, for example, two types of objects such as beads and dry powder. In some instances, the acoustic dispenser further comprises a membrane for separating one type of object from the other based on size, the separating membrane being between the vessel and the surface for deposition, whereby one type of object is separated from the other prior to deposition on the surface. Additionally, in some embodiments, the objects, such as particles, are electrostatically charged.

The acoustic dispenser of the present invention can be made using various types of components. For example, the vibrating means can be a speaker, a mechanical vibrator, or an electrical vibrator. The membrane of the acoustic dispenser for application of acoustic vibration preferably includes a dielectric layer and a conductive layer. In certain embodiments, the conductive layer has multiple holes which are smaller than the objects. In preferred embodiments, the vessel of the acoustic dispenser has a shape that enhances uniformity of acoustic vibration.

In certain preferred embodiments, the acoustic dispenser further comprises a first conductor and a second conductor within the apparatus, the first conductor being located below the second conductor, the two conductors being electrically connected, wherein the two conductors are positioned within the apparatus such that the objects flow through the conductors prior to being dispensed.

In additional preferred embodiments, the vibration membrane of the acoustic dispenser comprises a dielectric layer, and the vessel comprises an interior surface, the dielectric layer and the interior surface being made of the same material. More preferably, every surface of the apparatus having contact with the objects during normal use of the apparatus is made of the same material or is made of materials having the same triboelectric characteristics.

The present invention also provides methods for depositing multiple objects on a surface, comprising: (a) providing an apparatus having a membrane and a vessel for holding the objects, the objects being on the membrane; and (b) vibrating the membrane of the apparatus, thereby propelling the objects toward a substrate for deposition. In these methods, preferably the vibration is acoustic. Further, the objects are preferably beads or particles in a dry powder, such as a powder comprising a pharmaceutically active ingredient.

BRIEF DESCRIPTION OF THE DRAWINGS

FIG. 7A shows a vibrating membrane in the form of a mesh for dispensing larger objects without a carrier for imparting a triboelectric charge. FIG. 7B shows a solid vibrating membrane for dispensing smaller objects with a carrier for imparting a triboelectric charge.

DETAILED DESCRIPTION OF THE INVENTION

For purposes of this application, the following terms have the indicated meanings.

Acoustic dispenser: an apparatus for dispensing particles that employs vibration having a frequency in the acoustic (audible) range.

Chuck: a clamp for holding an object or objects.

Chuck for positioning objects: a chuck having a configuration that can be used for substantially arranging objects on the chuck in a selected pattern.

Electrostatic chuck: a clamp for holding an object or objects using electrostatic force.

Mechanical chuck: a chuck that uses compression to hold an object.

Non-mechanical chuck: a chuck that does not use compression to hold an object, including but not limited to a chuck that uses electrostatic or vacuum (i.e., negative pressure) means for such holding.

Object: a material thing.

Particle: an object equal to or less than about one millimeter in width or diameter.

Polarity Discriminator: two or more conductors that are electrically connected, and which provide differential treatment of objects, based on the polarity of the object's charge.

Recipient substrate: an object having a surface or layer that is coated with or will receive a coating of objects, such as particles, dispensed by the acoustic dispenser.

Separation membrane: a membrane in the acoustic dispenser, other than the vibration membrane. In certain applications, this membrane is optionally used for separating objects by size. The separation membrane need not actually be used for separation since it can be used, for example, as one of the conductors of a polarity discriminator.

Substrate: a surface or layer.

Vacuum chuck: a clamp for holding an object or objects using negative pressure.

Vibrating membrane: a membrane in the acoustic dispenser that is subjected to vibration.

1. Uses of the Acoustic Dispenser

The present invention provides an acoustic dispenser, which is an apparatus for dispensing objects, the apparatus using vibration having a frequency in the acoustic (audible) range. The use of an acoustic dispenser affords several advantages over the use of air to propel an object, such as a powder, for deposition. The advantages include the movement of particles in a directed manner rather than in a random manner, and a decrease in the amount of powder lost. Additionally, for example, the acoustic dispenser provides the ability to use an enclosed environment within the acoustic dispenser to deposit objects, which can be particularly advantageous when exposure to the objects is harmful to humans. Furthermore, for example, the acoustic dispenser can itself be used to tribocharge the objects to be dispensed, which provides for greater efficiency and is advantageous over corona charging, which can potentially alter the chemical nature of the objects.

In one aspect, the present invention provides an apparatus for depositing objects on a surface, comprising (a) a source of acoustic vibration; (b) a membrane for the application of acoustic vibration; and (c) a vessel for holding the objects. The acoustic dispensers of the invention can be used to create a powder cloud, for example, for application onto a substrate.

In another aspect, the present invention provides methods for depositing multiple particles on a surface, comprising (a) providing an apparatus having a membrane and a vessel for holding the particles, the particles being on the membrane; and (b) vibrating the membrane of the apparatus, thereby propelling the particles away from the membrane toward a surface for deposition. This method can be used, for example, to more accurately deposit a pharmaceutically active ingredient in the form of a powder onto a substrate such as a tablet, particularly when the active ingredient is present in a low dosage.

The acoustic dispenser of the present invention can be used, for example, in methods of chemical or pharmaceutical manufacturing, such as methods that require coating a recipient substrate with particles, the substrate being used to manufacture a chemical or pharmaceutical composition. For example, the acoustic dispenser can be used to coat a tablet with a powder. In preferred embodiments, the particles comprise a pharmaceutically active ingredient.

The acoustic dispenser can also be used to dispense larger objects, such as the tablets themselves. The maximum size of the objects dispensed by the acoustic dispenser can be larger than the dispenser itself, with the size and density of the object determining whether it can be dispensed.

The acoustic dispenser of the invention can also be used for the application of a design, such as a candy coating on an edible substrate. Alternatively, for example, the acoustic dispenser can be used for the application of a dry powder paint.

The acoustic dispenser can also be used, for example, to dispense beads for use in a chemical reaction, such as in combinatorial chemistry performed on a microtiter plate. The beads are preferably dispensed onto a chuck and can be positioned, for example, using the chucks described in co-pending application U.S. Ser. No. 08/630,012, filed Apr. 9, 1996, entitled "Chucks and Methods for Positioning Multiple Objects on a Substrate."

In certain preferred embodiments, the objects to be dispensed are charged prior to their application. The charge can be, for example, either a plasma charge or an electrostatic charge, depending upon the nature of the object. For instance, when dispensing beads, either a plasma or electrostatic charge can be used since neither causes damage to the bead. For other objects that may be damaged by plasma charging, electrostatic charging is preferably used. For example, a powder can be charged by admixture with carrier beads. Preferred beads for use in charging include Teflon-coated steel beads (Nu-Kote, Derry, Pa.) and Kynar-coated steel beads (Vertex Image Products, Yukom, Pa.), which are preferably about 100 microns in diameter.

2. Configuration of the Acoustic Dispenser

One embodiment of the acoustic dispensers of the invention is shown in FIG. 1. According to this figure, the acoustic dispenser 1710 has a speaker 1720 within a container 1730. On top of the speaker 1720 is a conductive layer 1740. On top of this layer 1740 is a dielectric layer 1750. On top of the dielectric layer 1750 is a membrane 1760, which is composed of a conductive layer and a dielectric layer, with the dielectric layer facing the outside and in contact with the particles (not shown) propelled by the membrane 1760.

Alternatively, for example, the structure of the acoustic dispenser is simplified in preferred embodiments, such as the diagram depicted in FIG. 5 which illustrates a container 2110 holding the objects 2120 which are propelled by the membrane 1760, the speaker (not depicted) being below the container 2110.

Preferred materials for use in making an acoustic dispenser according to the present invention are as follows. The container for holding the objects is preferably made of glass or polytetrafluoroethylene ("TEFLON") or another dielectric material. Preferably, the membrane for acoustic vibration includes a dielectric layer on top of a conductive layer. For example, polyimide or polytetrafluoroethylene ("TEFLON") can be used for the dielectric layer and copper can be used for the conductive layer. When made of polytetrafluoroethylene, the dielectric layer is preferably about 15 mils in thickness. Preferably, the dielectric layer is on the side exposed to the objects to be vibrated.

The vessel holding the objects is preferably made of a material that will not absorb the objects, such as glass or another triboelectrically compatible material that does not substantially charge the powder opposite in polarity to the charge on the powder due to the beads. In preferred embodiments, the vessel of the acoustic dispenser has a shape that enhances uniformity of acoustic vibration. See, for example, FIG. 1.

A. Vibration Membrane

The vibration membrane 1760 is further illustrated in FIG. 2, which illustrates the objects 1810 on top of the vibration membrane 1760, which is shown as it is vibrating back and forth. This vibration membrane, which does not have multiple holes extending through the conductive layer, is preferred for use with particles less than about 10 microns in average diameter.

In certain embodiments of the invention, the vibration membrane is made of one layer of a dielectric material. For example, the membrane can be made of one dielectric layer when the objects to be dispensed do not adhere to the vibration membrane and the use of electrostatic energy is not required in order to dispense the objects. In preferred embodiments, particularly when the objects have a tendency to adhere to the vibration membrane, there is at least one conductive layer in the vibration membrane. For example, the lower layer of the vibration membrane can be a conductive layer and the upper layer, in contact with the objects to be dispensed, can be a dielectric layer. A metal, for example, can be used to form the conductive layer and polytetrafluoroethylene ("TEFLON"), for example, can be used as the dielectric layer.

Preferably, the conductive layer of the vibration membrane has a hole in the center without the conductive material, thereby forming a ring of conductive material on the edges of the membrane. For example, with a 5 inch membrane, preferably a circular area having a diameter of about 4 inches has the conductive material removed. Alternatively, for example, multiple rings without conductive material can be formed in the conductive layer. These multiple rings can have the same or different potential, and can be electrically connected or floating. Structures other than a ring, including, for example, a square, can be used, but a circular structure is preferred, particularly for uniformity of dispensing the objects.

Without being limited to a particular theory, it is believed that the use of a vibration membrane in which the conductive material is located on the edges in the form of a ring assists in repelling the charged objects from the edges, thereby drawing the objects to the center of the vibration membrane. Once the objects are drawn to the center of the membrane, they are more efficiently propelled upwards to be dispensed.

In another aspect of the present invention, when the acoustic dispenser is used with objects having an average diameter greater than about 10 microns, and in certain embodiments, less than about 5 mm, the membrane for the application of acoustic vibration preferably comprises three layers. The top or uppermost layer is a conductive layer, which is preferably a mesh having multiple holes which are smaller than the average diameter of the objects, and more preferably smaller than the minimum diameter of the objects. Alternatively, for example, the mesh can be woven, with the spaces in between the rows and columns being smaller than the average diameter of the particles. The mesh can be made of a metal, for example, such as stainless steel, silver or copper. For example, a number 270 stainless steel mesh from Newark Wire Cloth Co. (Newark, N.J.) is preferably used with a particle having an average diameter of about 150 microns.

The second or middle layer of the vibration membrane is a dielectric layer. The dielectric layer can be made of any dielectric material with high dielectric strength, including, for example, polyimide and polytetrafluoroethylene ("TEFLON"), and it is preferably ductile and provides for resistance to wear. The bottom layer is a lower conductive layer, preferably without holes extending through it, and can be made of a metal, for example, such as silver or copper.

Optionally, a fourth layer, for example, can be added to the membrane, such as a thin polytetrafluoroethylene layer coated onto the wires of the mesh, and preferably is layered over both the wires and the gaps in the mesh. In addition to polytetrafluoroethylene, other dielectrics can be used, the dielectric preferably having substantially the same triboelectric characteristics of the powder to be charged. A power source is connected to the membrane and preferably about 2000 volts is applied during operation.

Without being bound to a particular theory, it is believed that the larger particles or other objects to be deposited by the acoustic dispenser can carry more than one charge due to local charging in particular areas of the particle. It is believed that the mesh of the membrane in the acoustic dispenser generates multiple fringing electric fields on the edges of the holes of the mesh which polarizes the particles and enhances the tribocharging process. Additionally, the fringing fields will cause a particle having a charge opposite to the charge of the majority of particles to become trapped, and eventually become charged correctly. Thus, the construction of a three-layered membrane, using for example, a conductive mesh, enhances the tribocharging of the particles, and enhances the charge uniformity of the particles by orienting the charges on the particles in substantially one direction.

Referring to FIG. 6A, the membrane 2210 for acoustic vibration has a lower conductive layer 2220 with a dielectric layer 2230 on top of it. On top of the dielectric layer 2230 is a conductive layer 2240, which is illustrated as a mesh. A top view of the mesh 2240 is shown in FIG. 6B. An alternative construction is shown in FIG. 6C, in which the upper conductive layer 2240 has holes 2250 in it rather than being a wire mesh.

B. Separation Membrane

In certain preferred embodiments in which the objects used with the acoustic dispenser comprise two types of objects, such as carrier beads and a powder, and the acoustic dispenser further comprises a separation membrane for separating one type of object from the other. Preferably, the separation membrane is located between the vessel and the surface for deposition, whereby one type of object is separated from the other based on size prior to deposition on the surface.

Thus, for example, the acoustic dispenser can be used to deposit a tribocharged powder that has been electrostatically charged through admixture with beads, the dispenser having a separation membrane that permits the powder to be deposited but causes the beads to remain within the dispenser. In certain preferred embodiments, this powder contains a pharmaceutically active ingredient, and is deposited onto a substrate, such as tablets.

Referring again to FIG. 1, above the vibration membrane 1760 for acoustic vibration is a separation membrane 1770, such as a mesh, for separating out objects having more than one size. As illustrated in FIG. 3, the separation membrane 1770 allows only smaller particles 1910, such as particles of a powder, to pass through, leaving larger particles 1920, such as carrier beads, behind it.

The separation membrane is preferably a #270 mesh (Newark Wire Cloth Co., Newark, N.J.) for particles from about 4 to about 6 microns in diameter and preferably a #200 mesh (Newark Wire Cloth Co., Newark, N.J.) for particles greater than about 6 microns.

Preferably, the separation membrane is at least about one-half inch from the vibration membrane, and they are preferably from about one-half to about three inches apart, and more preferably, from about one to about three inches apart. Preferably, the distance between the substrate for receiving the vibrating objects and the membrane for separating the objects is at least about 1 inch. The distance between the substrate and the vibrating membrane should be far enough to provide for uniformity of powder density, yet sufficiently near so that the kinetic energy needed to propel the objects is not dissipated.

Referring once again to FIG. 1, the separation membrane 1770 is attached to a container 1780 for the objects (not shown), and the container 1780 has a design that enhances acoustic vibration, as shown. Above the separation membrane 1770 is a substrate 1790, for receiving the objects that are dispensed. The substrate 1790 can be, for example, a substrate attached or adhered to an electrostatic chuck.

Preferably the membranes of the acoustic dispenser are cleaned between uses.

3. Vibrating Means

Preferably, the vibrating means in the acoustic dispenser is a speaker or multiple speakers, or more preferably, a piezoelectric device. The speaker can be any selected size, and is preferably about 20 watts. In other embodiments, the vibrating means is a mechanical vibrator, such as a piston, in which the frequency of vibrations lies within the audible (acoustic) range. Alternatively, for example, the vibrating means can use electrical energy, such as a motor with a low number of revolutions per minute. Preferably, the vibrating means is operated at the resonant frequency of the vessel holding the objects, which provides for the maximum amplitude of vibration of the membrane. Preferably, the acoustic frequency is stable during the deposition of objects.

Preferably a magnetic shield is used if the speaker used to vibrate the membrane has a magnet or non-magnetic beads are preferably used.

4. Continuous Operation of the Acoustic Dispenser

A. Vibrating Means

In certain preferred embodiments, such as those aspects of the invention in which the acoustic dispenser is used for large-scale manufacturing, more than one vibrating means or a single large vibrating means is used with the acoustic dispenser. Thus, the acoustic dispensers of the invention can be used for continuous operation in addition to batch operation. One example of the use of acoustic dispensers of the invention in large-scale manufacturing is the deposition of a pharmaceutically active ingredient onto tablets or other pharmaceutical substrates.

Continuous operation is particularly preferred since the use of the acoustic dispenser is believed to involve several stages. At first, the charge:mass ratio increases until it reaches a stable ratio. The achievement of a stable charge-:mass ratio optimizes the operation of the acoustic dispenser. Once the objects begin to be depleted, however, the charge-:mass ratio begins to increase again. Therefore, it is preferable to operate the acoustic dispenser without depleting the objects, with a continuous supply of charged objects. The continuous operation permits the use of the dispenser with a stable charge:mass ratio.

In one embodiment, multiple speakers are used, in parallel, in the acoustic dispenser, as shown in FIGS. 8A (side view) and 8B (top view). The speakers are synchronized and are located underneath a vibration membrane clamped by a grid. The speakers are preferably attached to the grid, for example, by bolting them. Preferably, there are two grids with the vibrating membrane between them. Each speaker generates a separate distribution of objects, such as a powder cloud. The overall powder cloud generated by multiple speakers is more uniform since each speaker will also vibrate objects received from adjacent speakers. This configuration provides the ability to lower the maximum amplitude of vibration of the membrane, and provides for more even distribution of the objects over the entire membrane, thereby creating greater uniformity.

Alternatively, for example, a single vibrating means can be used for continuous operation in large-scale manufacturing, as shown in FIG. 9. Using a single mechanical shaker that is electrically powered, the entire vibration membrane is shaken at a single frequency to generate a more uniform powder cloud. Preferably, the vibration membrane used in this embodiment is a thicker membrane that can withstand the force of mechanical shaking. Preferably, the thickness of the membrane is at least about 0.06 inches thick, and the membrane is preferably made of an insulating dielectric material such as polytetrafluoroethylene.

B. Loading of Objects and Carriers

In the continuous operation of an acoustic dispenser of the invention, the objects to be dispensed and the carriers, if any, are continuously loaded into the dispenser. Continuous loading is particularly preferred since it leads to greater uniformity of deposition of the charged objects. Furthermore, continuous loading leads to greater control of the charge:mass ratio of the objects.

Preferably, the objects to be charged are added gradually to the carriers that impart the charge. It is believed that this gradual addition will cause the objects to have greater contact with the carriers and less contact with each other, thereby promoting a more accurate charge with fewer objects receiving a charge of the wrong polarity.

According to certain embodiments of the invention, the carrier, such as a bead, that imparts a triboelectric charge, and the objects to be dispensed, such as a powder, are separately introduced into a mixer. The rate of introduction of beads and powder are separately controlled. The mixer then loads the bead/powder mixture into the acoustic dispenser. See, for example, FIGS. 10A and 10B. According to FIG. 10A, the powder and carrier beads are mixed in reservoir 1 and then added to a reservoir 2 containing only powder coated carrier beads, which are constantly shaken. The reservoir 1 containing the mixture of beads and powder is illustrated in greater detail in FIG. 10B, which shows the separate introduction of beads and powder into the mixture, which is continuously shaken. The bead and powder mixture is then added to the vibration membrane 3 of the acoustic dispenser, and subjected to the polarity discriminator 4 (described in Section 6 below) prior to release from the dispenser.

According to FIG. 10B, reservoir 1 is filled with beads from a bead injector 6, and powder is gradually introduced via a powder feeder 8. The beads and powder are shaken and then dispensed through conduit 10 to the reservoir 2 containing only carrier beads coated with powder. Preferably, reservoir 1 has a conductive plate on the bottom of the reservoir. Without being limited to a particular theory, it is believed that the powder coated beads will be electrostatically attracted to the bottom of reservoir 1, thereby leading them to be fed to reservoir 2 through conduit 10 located near the bottom of reservoir 1.

5. Circuit Diagram and Mathematical Theory of Dispenser

A circuit diagram of the acoustic dispenser shown in FIG. 1 is illustrated in FIG. 4. Referring to FIG. 4, the oscillator $O_{sc}$ provides a single frequency oscillation for the audio amplifier $A_{mpl}$ to couple energy to the speaker $S_p$. The oscillator $O_{sc}$ can be, for example, a single chip with tuning components.

Without being limited to a particular theory, the following mathematical formulas can be used to evaluate the force of propulsion of particles or other objects by the acoustic dispenser.

If the membrane is vibrating at an audible frequency, the motion at any point of the membrane can be described using the following equations:

$$z(t) = A\sin(\omega t)$$

$$v(t) = \frac{dz}{dt} = A\omega\cos(\omega t)$$

$$a(t) = \frac{d^2 z}{dt^2} = -A\omega^2\sin(\omega t)$$

where A is the amplitude of vibration, z is the average displacement from any one position, v is the velocity, a is the acceleration and ω is the angular velocity of the wave.

For example, in a membrane, if A=2 mm and ω=600; the peak 'w' and 'a' will be 1.2 $ms^{-1}$ and 720 $ms^{-2}$, respectively. An object at rest on the membrane will leave the membrane at a velocity smaller or equal to the peak 'v'. At a leaving velocity of 1.2 $ms^{-1}$, the object will reach a height of 7.35 cm before falling. If a mesh is placed in the path of the object, the object will hit the mesh and cause a momentum transfer. If the object is a tribocharged bead with some attached powder, the momentum will be transferred to the powder. FIG. 3 schematically illustrates this action. As the bead 1920 and the powder 1910 are tribocharged, the powder 1910 escaping from the container will be charged. Inside a container, the amplitude of the vibration of the membrane can be maximized by operating the speaker at the resonant frequency of the container.

6. Discrimination of Polarity of Charged Objects to be Dispensed and Shuttering the Dispensing of Charged Objects Without being limited to a particular theory, it is believed that, during the operation of the acoustic dispenser, the objects to be dispensed will rub against one another as well as with a carrier for triboelectrically charging the objects. Depending upon the triboelectric nature of the objects to be dispensed, this could result in the some of the objects being incorrectly charged (charged with a polarity that is the opposite of the polarity of objects charged by the carrier). This can lead, for example, to objects adhering to one another, which can cause undesirable results, such as clumping or error in deposition.

Figure 1:
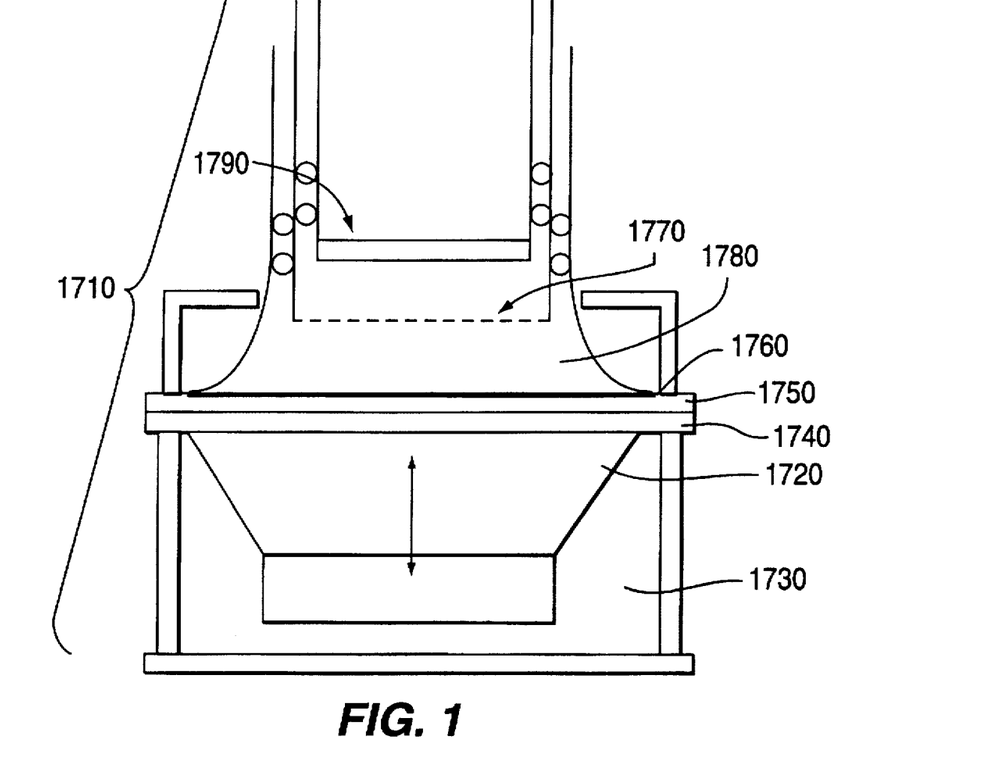
FIG. 1 is a cross-sectional schematic view of an acoustic dispenser according to the present invention.
Figure 2:
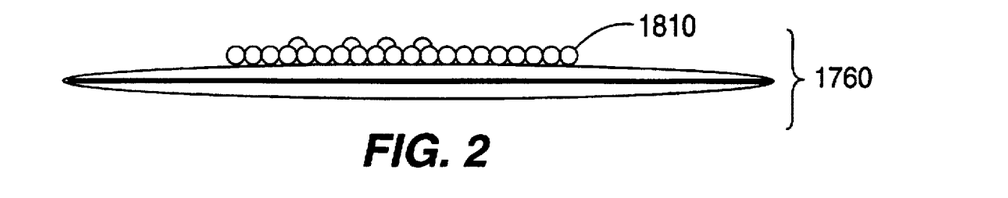
FIG. 2 is a cross-sectional schematic view of the membrane of an acoustic dispenser according to the present invention.
Figure 3:
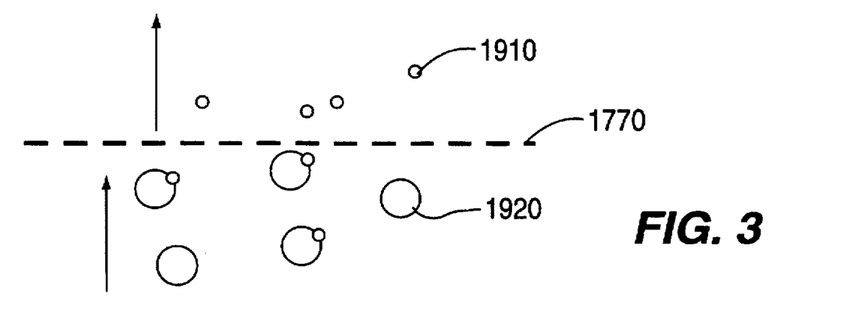
FIG. 3 is a cross-sectional schematic view of a mesh for separating objects within an acoustic dispenser of the present invention for dispensing objects less than about ten microns.
Figure 4:
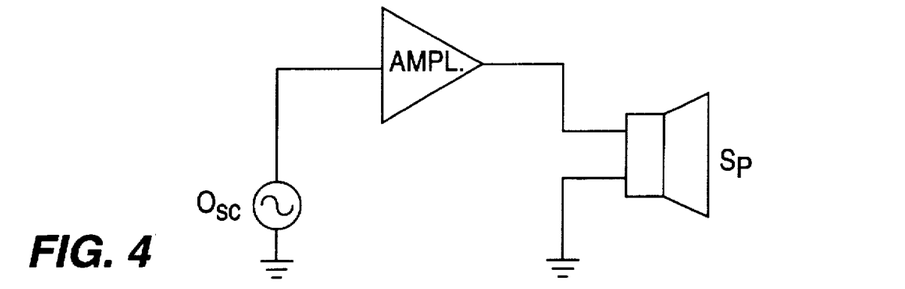
FIG. 4 is a circuit diagram of an acoustic dispenser according to the present invention.
Figure 5:
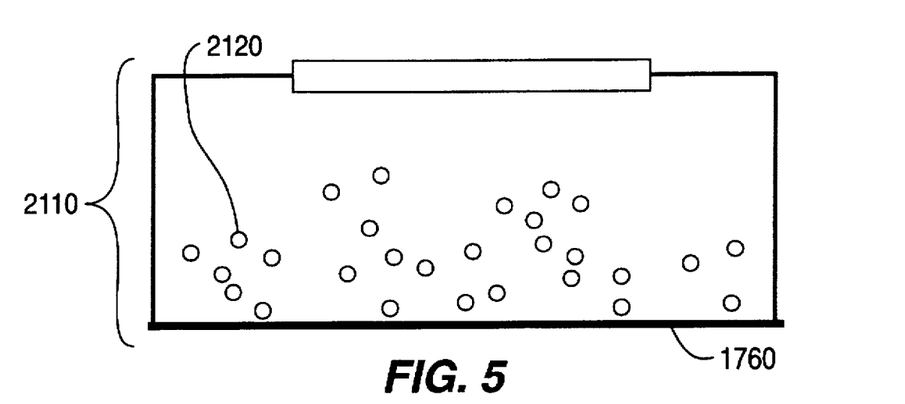
FIG. 5 is a cross-sectional view of a schematic representation of an acoustic dispenser according to the present invention.
Figure 6A:
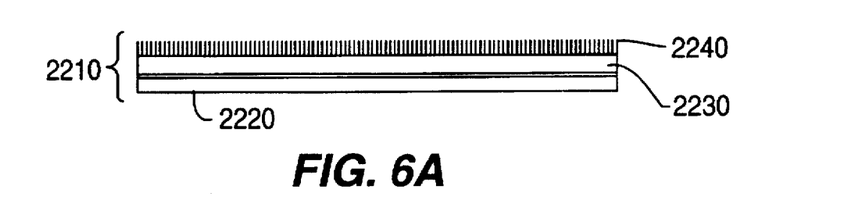
FIG. 6A is a cross-sectional view of a schematic representation of a mesh membrane of an acoustic dispenser according to the present invention, for dispensing objects greater than about ten microns in diameter.
Figure 6B:
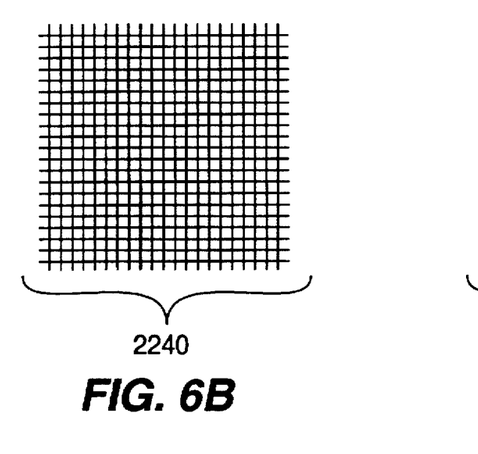
FIG. 6B is a top schematic view of a mesh membrane of an acoustic dispenser according to the present invention, for dispensing objects greater than about ten microns in diameter.
Figure 6C:
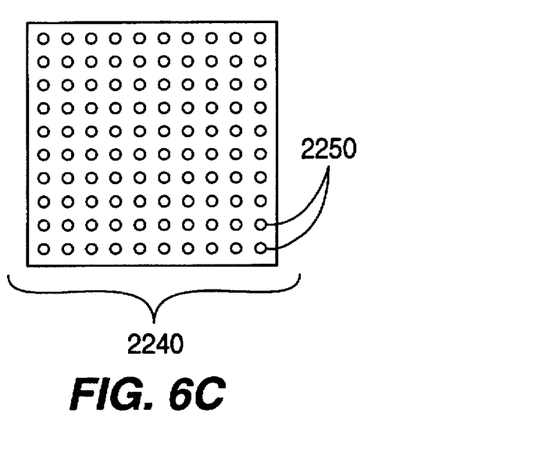
FIG. 6C is a top view schematic of a solid membrane with holes in it for an acoustic dispenser according to the present invention, for dispensing objects greater than about ten microns in diameter.
Figure 7A:
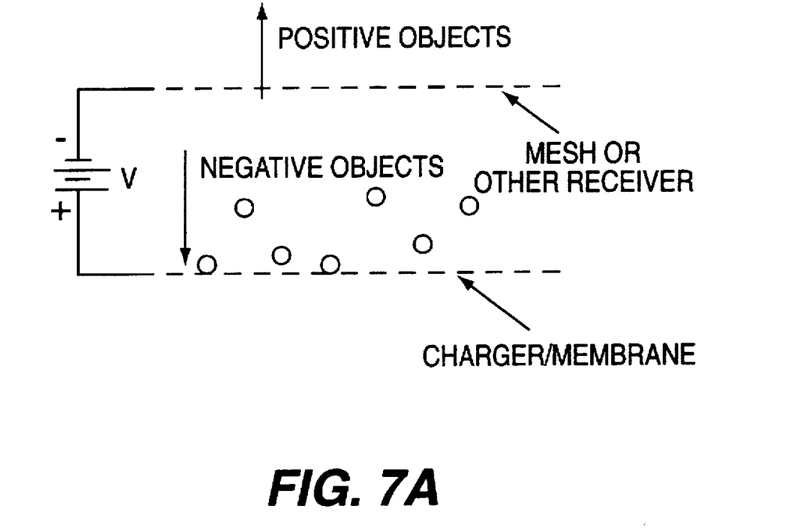
FIGS. 7A and 7B are diagrammatic cross sections of acoustic dispensers of the invention having a polarity discriminator formed by electrical connection of a vibration membrane and a separation membrane.
Figure 7B:
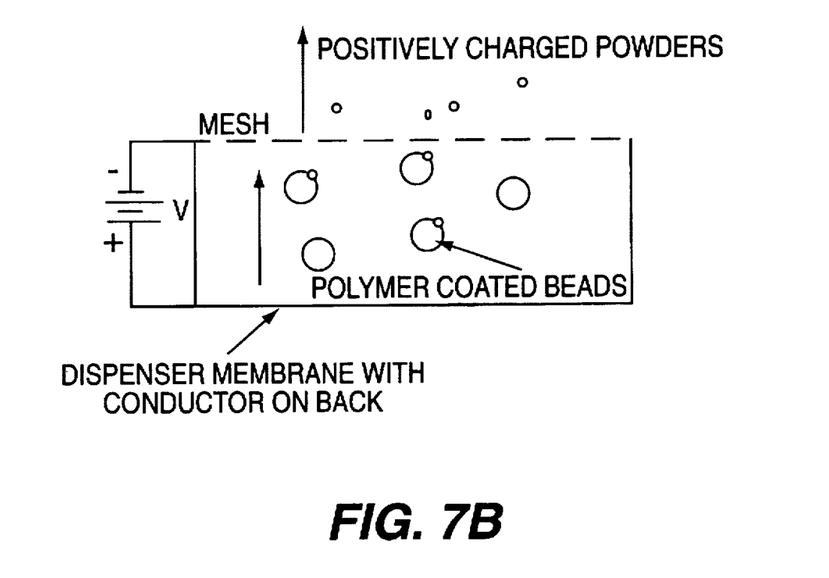
Figure 8A:
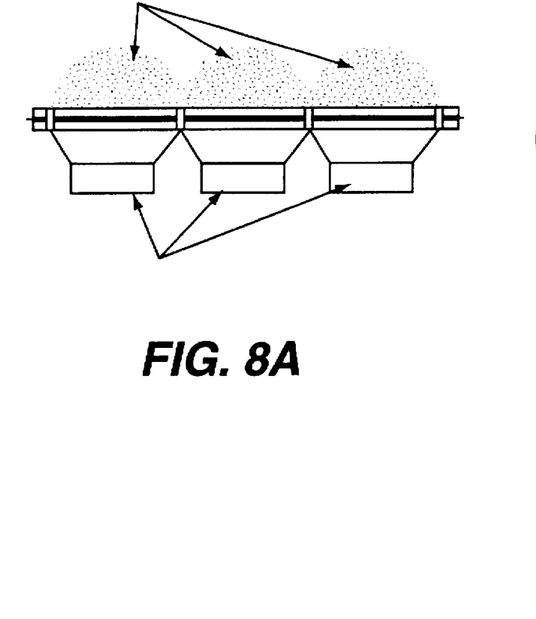
FIGS. 8A and 8B show a diagrammatic cross section and a top view, respectively, of speakers connected in parallel in an acoustic dispenser of the invention.
Figure 8B:
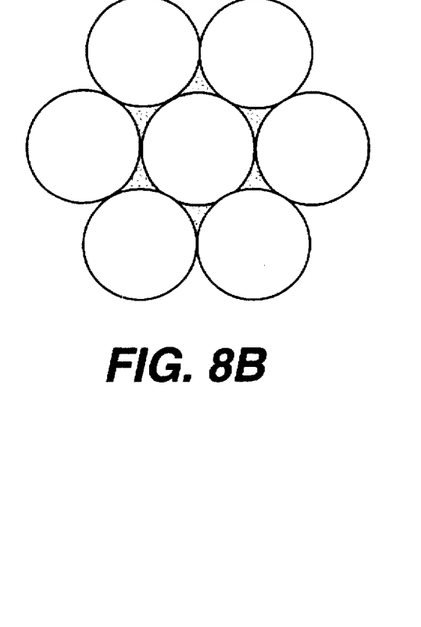
Figure 9:
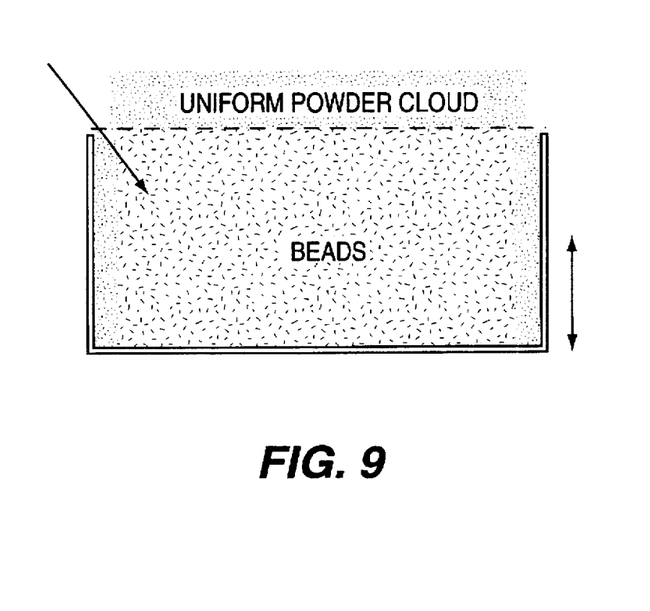
FIG. 9 shows a diagrammatic cross-section of acoustic dispenser of the invention having a mechanical vibrating means.
Figure 10A:
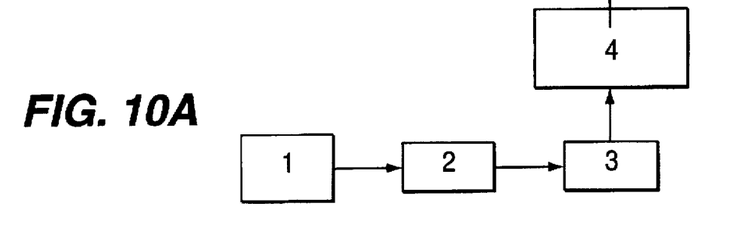
FIG. 10A is a diagrammatic representation of a preferred flow chart with several components for providing charged objects to the acoustic dispenser of the invention.
Figure 10B:
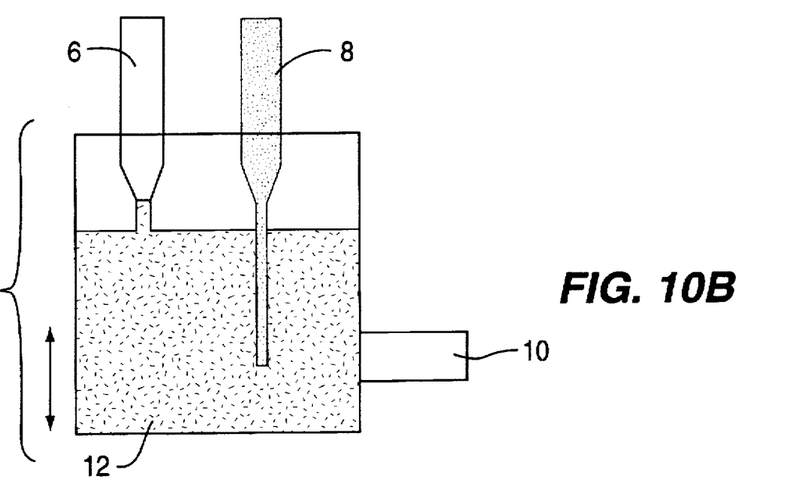
FIG. 10B shows a diagrammatic cross-section of a component of the acoustic dispenser for mixing a carrier, such as beads, with the object to be deposited, such as a powder.
Figure 11:
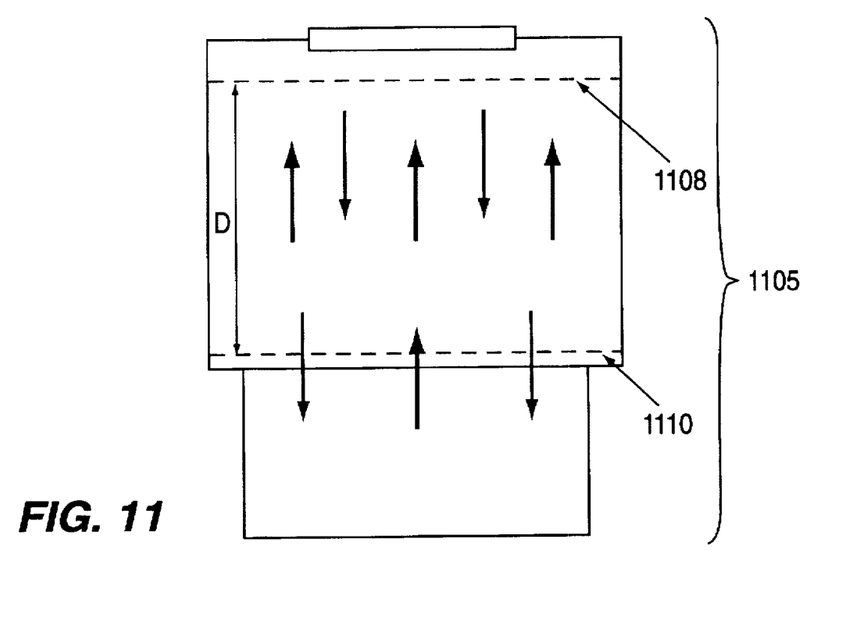
FIG. 11 is a diagrammatic cross-section of an acoustic dispenser of the invention having a polarity discriminator which causes certain objects to be propelled upwards and other objects to be retained, based upon the polarity of the object's charge.

To overcome the foregoing potential problems, it is preferable to electrically connect a conductor within the acoustic dispenser to at least one other conductor. Optionally, more than two conductors can be connected in series. The following description of a polarity discriminator/shuttering means is applicable not only to acoustic dispensers of the invention, but also to other apparatuses in which the orientation of charged objects according to polarity or a shuttering means is desired.

For example, a conductive layer on the vibration membrane can be electrically coupled to a conductive separation membrane within the acoustic dispenser. Without being limited to a particular theory, it is believed that coupling two conductors generates an electric field whereby, for the most part, only objects with the correct charge are propelled from the dispenser. For example, if positively charged objects are to be dispensed, the vibration membrane is positively charged to attract wrongly charged (negatively charged) objects. The separation membrane, which is encountered by the objects before exiting the dispenser, is negatively charged to attract the correctly (positively) charged objects, so that they are dispensed.

Furthermore, the polarity discriminator formed by connecting two or more conductors serves to substantially prevent the dispensing of a particle or other object with a charge:mass ratio below a selected value, equal to gD/V, where "g" is the gravitational constant, "D" is the distance between the two conductors and "V" is the potential difference across the two conductors. The objects having a lower charge:mass ratio will ultimately become sufficiently charged after sufficient contact with the triboelectrically charged carriers inside the acoustic dispenser. See, for example, FIG. 11, which shows an acoustic dispenser of the invention 1105 having a polarity discriminator 1110 which causes certain objects (not shown) to be propelled upwards and other objects to be retained, based upon the polarity of the object's charge.

Thus, electrically connecting these two conductors provides a mechanism for enhancing the stability of the average charge:mass ratio for the entire tribocharged mixture. Furthermore, this connection enhances the deposition of the charged objects dispensed from the acoustic dispenser onto selected charged areas of an electrostatic chuck, for example, such as a chuck designed for positioning and transporting beads or other objects.

Further, the two conductors can be charged in the opposite polarity to repel objects of the opposite charge, for example, during cleaning of the acoustic dispenser.

The relative potential of the two conductors determines whether the space between the conductors will discriminate between objects having a different charge polarity. If the relative potential is sufficiently large, the substantial majority of objects leaving the dispenser will carry a charge of the same polarity. If, for example, q/m is 1 μC/g and d is 3 cm, than V is preferably greater than or equal to about 300 volts.

Alternatively, two electrically connected conductors can function as a shuttering means for the dispenser, abruptly terminating the dispensing of objects by trapping the objects in the space between the two conductors. One of the advantages of this shuttering action is the ability to quickly terminate dispensing the objects, the termination being much faster than most mechanical mechanisms.

The conductive material onto which the powder will be applied also provides the opportunity for setting up an electric field with respect to the dispenser to further discriminate against incorrectly charged objects or to act as a shutter. Furthermore, more than two conductors can be connected in series to enhance the discrimination of polarity or shuttering. For example, the vibration membrane, the separation membrane and the tablet represent three conductors that can be connected in series for charge discrimination or shuttering. For instance, the vibration membrane can be placed at 0 volts, the separation membrane at −500 volts and the tablet (on an electrostatic chuck) at −2000 volts. If a positively charged object is selected to exit the dispenser, then the vibration membrane, which is the lowest conductor geographically with respect to the acoustic dispenser, has a higher potential. The geographically uppermost conductor is the conductive substrate, such as a tablet, onto which the powder is deposited. If a negatively charged object is selected, the geographically lowest conductor has a lower potential.

An illustration of an electrical connection between two conductors that provides for discrimination of charged objects based on polarity (a "polarity discriminator") is provided in FIG. 11. According to FIG. 11, an acoustic dispenser 1105 is shown in which a voltage potential is generated between a first conductor 1110, such as the vibration membrane, and a second conductor 1108, such as a separation membrane.

By means of illustration, in order to propel a sufficient number of beads to an electrostatic chuck for attracting beads, the surface of the lower layer of the membrane is preferably grounded, the surface of the separating membrane is preferably at 3000 volts, the surface of the upper conductive layer of the chuck is preferably grounded and the lower electrode of the chuck is preferably −1500 volts.

Without being limited to a particular theory, if a charged object passes through a region of the electric field formed by the two conductors, the object must overcome gravity in order to go through that region. The following equation applies:

$$Eqd+\frac{1}{2}mv^2=mgd,$$

where V is the potential of the capacitor formed by the two conductors, E is the electric field, v is the velocity of the object, d is the thickness of the region inside the capacitor, m is the mass of the object and q is the charge of the object.

If the electric field accelerates the object, the following equation applies:

$$|Eqd|\geqq mgd \text{ or } |V|\geqq gd(m/q).$$

For a charged particle cloud formed from a dry powder, particles with a low q/m value may not be able to generate sufficient energy from the electric field to overcome gravity. The potential V is preferably sufficiently large to cause the correctly charged particles to overcome gravity while retarding the wrongly charged particles.

In order for the electric field to act as a shutter to reverse, stop or trap the objects in the region between the conductors, the following equation applies:

$$|Eqd|\geqq \frac{1}{2}mv^2 \text{ or } |Vq|\geqq \frac{1}{2}mv^2.$$

If the potential V is small, objects of both polarities will be trapped in the capacitor since the attractive force of image charges on the conductors will be sufficiently large to adhere the objects to the conductors. Thus, the relative potential determines whether the capacitor acts to discriminate between objects based on polarity or acts as a shutter, ending the dispensing of objects.

An exemplary structure of an acoustic dispenser having a mechanism for shuttering or polarity discrimination, as described above, is shown in FIGS. 7A and 7B. FIG. 7A depicts the membrane for vibration 1760 that is electrically connected to a membrane for separation 1770. The vibration membrane 1760 shown in FIG. 7A is a mesh with multiple holes therein, preferably for use with particles having an average diameter greater than about ten microns. In contrast, the vibration membrane 1760 shown in FIG. 7B is a solid membrane, preferably for use with particles having an average diameter less than about ten microns.

According to FIG. 7A, there is no larger object, such as a carrier bead, to be separated from the objects 1910 to be dispensed. Nonetheless, this acoustic dispenser is equipped with a separation membrane that functions as a polarity discriminator or a shutter rather than for separation. In contrast, the separation membrane 1770 shown in FIG. 7B is used both for separation and as a polarity discriminator or shutter. According to FIG. 7B, a larger object 1920, such as a carrier bead, is separated from a smaller object 1910 to be dispensed.

7. Enhancement of Deposition on the Recipient Substrate

Figures 12A, 12B, 12C:
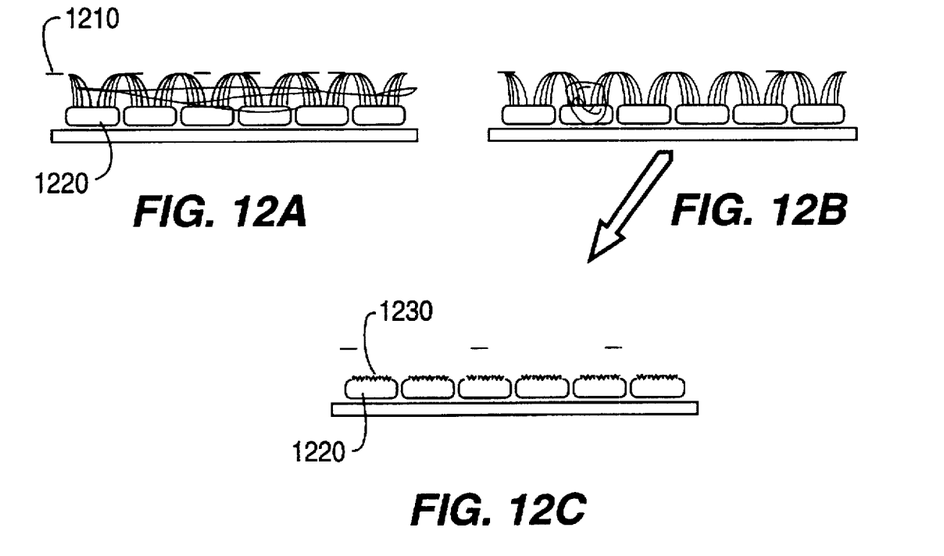
FIG. 12 is a diagrammatic representation of the use of a mesh placed above the recipient substrate upon which the objects are to be deposited, to direct the deposition of the objects.

In preferred embodiments, the accuracy of local deposition onto a recipient substrate is enhanced by generating a local electric field to guide the objects to be deposited. For example, a grid 1210 can be placed above the recipient substrates 1220 as shown in FIG. 12A. The grid is a conductive material, such as a metal, with multiple holes, each hole being aligned with each recipient substrate. The hole is preferably slightly smaller than the recipient substrate. This grid can be used, for example, with deposition of a powder 1230 onto multiple tablets 1220 as shown in FIG. 12C. The grid substantially prevents deposition on the edges of the tablets, thereby aiding in sealing the powder onto the tablet. The grid can optionally be electrically biased to enhance the directed deposition of objects.

Without being limited to a particular theory, it is believed that the electric field generated by the above-described grid will accelerate the objects being dispensed. For example, a particle having a charge:mass ratio of 3 mC/kg exposed to an electric field of 100 V/mm will experience a force corresponding to 30×gravity. An electric field greater than 500 V/mm can be used, for example. The use of the field enhances uniformity of deposition by guiding particles to different locations so that the electric potential is generally uniform. The field may therefore cause particles to deposit in monolayers which can be more accurately controlled. Thus, the field can used to provide more accurate deposition, for example, of a pharmaceutically active powder onto a tablet.

8. Feedback Control of Deposition

Preferably, the charge:mass ratio of the objects to be dispensed is measured during the deposition process to provide feedback control for termination of deposition when the desired number of objects have been deposited. For example, feedback control can be used to monitor deposition of a pharmaceutical powder until the appropriate dosage has been achieved.

Figure 13A:
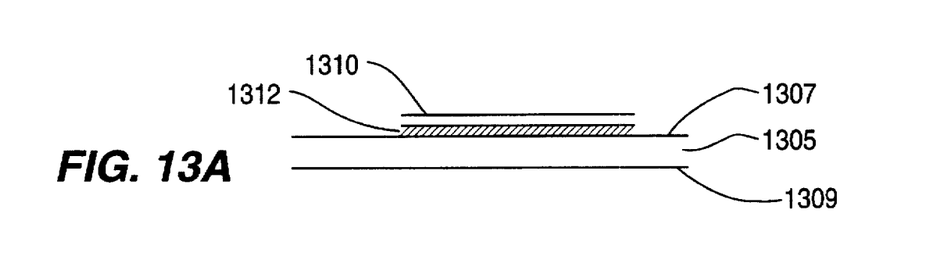
FIG. 13A is a diagrammatic cross-section of a modified quartz crystal monitor.
Figure 13B:
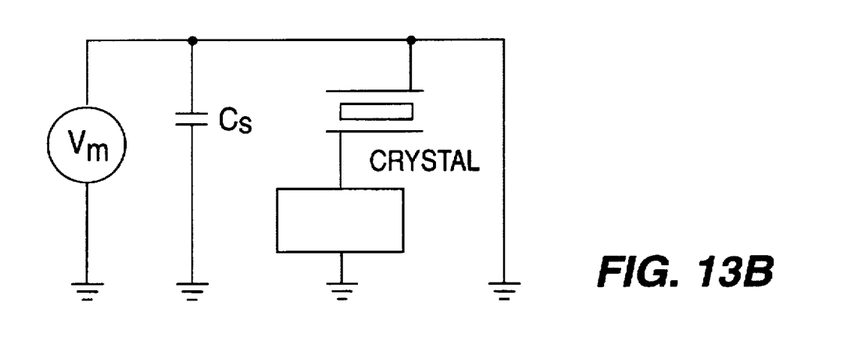
FIG. 13B is a circuit diagram of the monitor shown in FIG. 13A.

Average charge:mass ratio can be measured, for example, using a velocimeter and a modified quartz crystal monitor. Referring to FIG. 13A, the quartz crystal monitor 1305 has a top sensing layer 1307 and a bottom layer 1309 for connection to a meter. The quartz crystal monitor is modified by adding a charge sensing layer 1310, which is a second conductive layer, and a dielectric layer 1312, as illustrated in FIG. 13A. This modification causes the monitor to sense both charge and mass at the same time. See, for example, the circuit diagram of the monitor shown in FIG. 13B, in which Cs is the capacitor due to the dielectric layer, which measures the collected charge.

Preferably, at least two charge:mass monitors are used, one with the acoustic dispenser, and the other with the chuck or other means holding the recipient substrate or substrates.

9. Use of Acoustic Dispenser with a Sensing Electrode for Determining the Amount of Deposited Charge The electrostatic chucks described below, or other surfaces upon which a recipient substrate is located, optionally includes sensing electrodes to sense the amount of charge deposited on the recipient substrate. In certain aspects of the present invention, the amount of charge that can be deposited, for example, on an electrostatic chuck is limited to a finite number, and this limitation provides a mechanism for accurately determining the amount of powder deposited on the substrate held by the chuck. Alternatively, the amount of deposition may not be self-limiting. A sensing electrode can be used with the acoustic dispenser, for example, to determine the amount of powder deposited onto a tablet, wherein the powder includes a pharmaceutically active ingredient. Thus, the present invention provides a more accurate and uniform way of dispensing a selected amount of objects. For example, the invention provides for the accurate deposition of a selected amount of a pharmaceutically active ingredient deposited on a substrate, especially when the active ingredient is present in small doses.

10. Relative Humidity

In preferred embodiments of the present invention, relative humidity is controlled to provide optimized deposition of objects using the acoustic dispenser. Relative humidity affects the charging characteristics of the objects to be dispensed. If the relative humidity is too high, the objects may be too weakly charged. If the relative humidity is too low, the objects may become too highly charged and may aggregate.

While using the acoustic dispenser, the relative humidity is preferably from about 30% to about 60%. During the charging of the objects, the relative humidity is preferably from about 30% to about 40%, or such relative humidity that optimizes the charging of the objects without causing them to become incorrectly charged. During the deposition of the objects, the relative humidity is preferably from about 50% to about 60%, or such relative humidity that optimizes the ability to maintain the charge on the objects.

11. Objects for Use with the Dispenser

In certain preferred embodiments, the objects dispensed by the acoustic dispenser are particles in a micronized dry powder, which preferably comprises a pharmaceutically active ingredient. In one aspect, the acoustic dispensers of the present invention are used to deposit powder on a pharmaceutical substrate, such as a tablet. An electrostatic chuck can be used, for example, to hold the pharmaceutical substrate while the powder is deposited onto the substrate. Alternatively, for example, a vacuum chuck can be used to hold the substrate. The powder can be uniformly applied or applied using charge imaging, as described below and in co-pending application entitled "Electrostatic Chucks." More than one type of powder can be deposited, including more than one pharmaceutically active ingredient.

Preferably, the powder is in micronized form and the particles are at least about 1 micron in diameter. More preferably, a micronized powder will have particles ranging from about 4 to about 8 microns. Preferably, the powder is electrostatically charged before application to the acoustic dispenser, for example, through admixture with carrier beads such as by mechanical shaking, preferably for about 30 minutes. A particle greater than about 50 microns can be charged directly without the use of beads, but a smaller particle preferably has a carrier such as beads to charge the particle.

In order to impart desirable electrostatic characteristics onto an object to be dispensed by the acoustic dispenser of the invention, a material having such desirable characteristics can be added to or incorporated into the object. For example, a polyalkylene glycol, preferably polyethylene glycol (PEG), such as PEG 8,000 (molecular weight) can be mixed with a powder in order to charge the powder positively when mixed with a negative carrier, such as polytetrafluoroethylene. The characteristics of PEG are particularly favorable since it has higher conductivity than most organic molecules. PEG provides for a more uniform charge:mass ratio, thereby decreasing powder aggregation and enhancing uniformity of the powder cloud generated by the acoustic dispenser For example, PEG can be added to a pharmaceutically active powder. Since PEG is highly water soluble, the mixture can be dissolved in water, for example, dried and then micronized for application to the acoustic dispenser of the invention. PEG is also particularly advantageous for use with a pharmaceutical substrate since the sealing of the powder containing the active ingredient onto the substrate can be achieved at a lower temperature, with less likelihood of damage to the active ingredient. For example, the substrate can be heated at a lower temperature by adjusting the temperature to match the melting point of PEG. Further, with the use of infrared emissions, infrared energy matching the absorbance of PEG can be used, thereby causing PEG to absorb most of the heat generated from the infrared energy. The infrared heat can be monitored, for example, using a feedback control mechanism.

In addition to powders containing pharmaceutical ingredients, the present acoustic dispenser invention can be used, for example, with dry paint particles, phosphor powder, and any other particles or other objects that can be triboelectrically charged.

12. Recipient Substrates

Recipient substrates that can be coated using the acoustic dispenser of the present invention include, but are not limited to, pharmaceutical substrates suitable for human consumption, such as tablets, capsules or caplets, or for example, a microsphere for encapsulation within a capsule. In certain preferred embodiments, the recipient substrates are tablets. The recipient substrate can also be, for example, a water soluble film such as a hydroxypropyl methyl cellulose resin, or a thin conductive substrate such as an edible polymeric substrate, which can be used as a substrate for deposition of a pharmaceutically active powder, and the substrate can subsequently be used, for example, to create or coat a tablet. Thus, a tablet can be manufactured with an active ingredient, for example, by direct deposition onto the tablet itself, by deposition onto an edible substrate that is incorporated into the tablet, or by deposition onto a substrate (edible or inedible) which is subsequently transferred onto the tablet.

Other recipient substrates include suppositories, dressings, bandages and patches, as well as, for example, a container for an inhaler. The inhaler can be a flat, such as a ceramic disk upon which a plurality of medicament dosages are positioned. See, for example, U.S. Ser. No. 08/471,889, which is incorporated herein by reference. Alternatively, for example, the recipient substrate can be a tape used in an inhaler, which can be made of materials such as polytetrafluoroethylene, silicon, alumina ceramic, aluminized organic photoconductor, polycarbonate, polyimide or polyethylene. See, for example, co-pending application entitled "Inhaler Apparatus with Modified Surfaces for Enhanced Release of Dry Powders," filed simultaneously herewith.

Preferably, the tablets used as recipient substrates which are held by an electrostatic chuck include a substantial amount of cellulose, preferably greater than about 50% cellulose, more preferably greater than about 60% cellulose, even more preferably greater than about 75% cellulose, even more preferably greater than about 90% cellulose, and most preferably about 95% cellulose. In other embodiments, the tablets include about 65% lactose and about 34% cellulose. In certain embodiments, the tablets include about 80% lactose. Preferably, the tablets do not have an ingredient which would cause them to deviate from being either a good conductor or a good dielectric. For example, with a conductive tablet such as one that is substantially made of cellulose, preferably the tablet does not include dielectric metal oxides such as ferrous or ferric oxide or titanium oxide. Preferably the amount of iron oxide, if present, is less than about 1%. Additionally, the tablet preferably does not include moisture and preferably does not include a substantial amount of a salt such as sodium bicarbonate that becomes conductive with high humidity, thereby making the most efficient operation of the electrostatic chuck affected by humidity.

The tablets may optionally have additional components, including but not limited to sodium starch glycolate and magnesium stearate.

When an edible substrate, having for example, a pharmaceutically active powder deposited thereon, is fused with a tablet, preferably the edible substrate is made of substantially the same component as the tablet, such as cellulose. For example, hydroxypropyl methyl cellulose can be used, such as Edisol M Film M-900 or EM 1100 available from Polymer Films Inc. (Rockville, Conn.).

The deposition of particles on recipient substrates, such as the deposition of a pharmaceutically active powder on tablets, is particularly useful, for example, when the active ingredient is incompatible with the remainder of the tablet. Furthermore, more than one type of ingredient can be coated on an object, such as a tablet. The tablet can be further processed after the particles are deposited on it; for example, the tablet can be coated after deposition.

13. Use of Acoustic Dispenser with a Chuck for Holding Recipient Substrates

The acoustic dispenser of the present invention can be used together with a chuck, including the vacuum and electrostatic chucks described in co-pending applications U.S. Ser. No. 08/630,012, filed Apr. 9, 1996, entitled "Chucks and Methods for Positioning Multiple Objects on a Substrate" and U.S. Ser. No. 08/630,050, filed Apr. 9, 1996, entitled "Electrostatic Chucks," a continuation-in-part of which is filed simultaneously herewith. These chucks can be used to hold and/or position the recipient substrates that are coated with the objects dispersed from the acoustic dispenser of the present invention. Thus, for example, the acoustic dispenser can be used to deposit a pharmaceutically active powder onto tablets held by an electrostatic chuck. When the acoustic dispenser is used together with an electrostatic chuck, the deposition of particles shows greater uniformity, and provides for less waste of particles.

When using a chuck to hold a recipient substrate, such as a tablet, during deposition of particles, such as a powder containing a pharmaceutically active ingredient, the tablets are preferably closely packed on the chuck so that only the tablets receive the powder, and the chuck itself is not coated with powder.

The acoustic dispenser of the present invention can also be used together with an electrostatic chuck with floating electrodes for charge imaging, described in co-pending patent application Ser. No. 08/630,050 (entitled "Electrostatic Chucks," filed Apr. 9, 1996), a continuation-in-part of which is filed simultaneously herewith, and which is used to selectively attract particles to a substrate in contact with the floating electrodes. Briefly, an electrostatic chuck for charge imaging comprises three layers, preferably with an optional fourth layer. The bottom layer is the lower conductive layer, which is also known as the backing electrode. The second layer, on top of the lower conductive layer, is a dielectric layer. The third layer is an upper conductive layer on top of the dielectric layer, and this upper conductive layer has two types of electrodes, floating electrodes and shielding electrodes. In preferred embodiments, the floating electrodes are electrically isolated from the other conductors, and there is a gap between the floating and shielding electrodes. The fourth (optional) layer, on top of the upper conductive layer, is a dielectric layer, which is preferably the layer having contact with the medicament powder. Without being limited to a particular theory, it is believed that when a potential is applied across the shielding and backing electrodes, a charge redistribution occurs on the floating electrodes. This charge redistribution causes electrostatically charged objects to be attracted to the areas of the chuck corresponding to the floating electrodes, thus resulting in deposition in these areas. Preferably, there is a high fringing field in the gap between the floating and shielding electrodes, but this field is preferably not large enough to cause electrical discharge.

The floating electrodes of the charge imaging chuck determine the pattern of deposition of the medicament powder on the substrate, and hold the powder thereon. During the deposition of powder, the charge imaging chuck is electrically connected to a power source, which is subsequently disconnected after deposition. The floating electrodes can be configured, for example, to spatially determine individual dosages on a substrate.

Using an electrostatic chuck with floating electrodes to deposit powder onto a substrate, the amount of powder deposited on the substrate is determined by the charge or bias potential of the chuck, and only a finite amount of powder can be deposited. The amount of powder to be deposited can therefore be controlled by controlling the bias potential, and it is unrelated to the duration of deposition, once the limit has been reached.

Advantages of the use of the acoustic dispenser together with an electrostatic chuck for deposition of particles or other objects and for charge imaging include the ability to coat a substrate in a more accurate and more uniform manner, which is particularly important when the dosage of active ingredient is low, such as from about 1 μg to about 1 mg. Other low dosage ranges include for example, from about 1 μg to about 500 μg, from about 10 μg to about 250 μg, and from about 20 μg to about 100 μg, such as about 25 μg. Further, the use of the acoustic dispenser with an electrostatic chuck for deposition of particles and for charge imaging provides the advantage, for example, of a mechanism for applying an active ingredient to a pharmaceutical carrier that may be immiscible or otherwise incompatible with the active ingredient.

14. Carriers for Use in Tribocharging Objects

A. Materials

Examples of materials that can be used for tribocharging include polytetrafluoroethylene ("TEFLON"), and polymers of chlorotrifluorethylene, chlorinated propylene, vinyl chloride, chlorinated ether, 4-chlorostyrene, 4-chloro-4-methoxy-styrene, sulfone, epichlorhydrin, styrene, ethylene, carbonate, ethylene vinyl acetate, methyl methacrylate, vinyl acetate, vinyl butyral, 2-vinyl pyridine styrene, nylon and ethylene oxide. See, for example, "Triboelectrification of Polymers" in K. C. Frisch and A. Patsis, *Electrical Properties of Polymers* (Technomic Publications, Westport, Conn.), which article is hereby incorporated by reference in its entirety. For example, polytetrafluoroethylene and polyethylene and other negatively charged materials will create a positive charge on the object. Nylon and other positively charged materials will create a negative charge on the object.

In certain aspects of the present invention, the vibration of the membrane of the acoustic dispenser can itself provide sufficient friction between objects to cause tribocharging, and the objects need not be charged prior to the use of the acoustic dispenser.

B. Number of Beads

The objects to be dispensed by the acoustic dispenser, such as particles in a powder, can be electrostatically charged through friction, for example, by mechanically shaking a mixture of beads and a powder, preferably for about 30 minutes, and preferably with an amount of beads and powder that so that the surface area of the beads corresponds to the surface area of the powder, the surface area be determined by calculating $4\eta r^2$. For example, about 15 g of beads can be used for about 450 mg of powder, assuming the density is about 1 g/cc. The beads preferably are a conductive material, such as steel, coated by a dielectric, such as Teflon or Kynar. Teflon coated beads can be obtained, for example, from Nu-Kote (Derry, Pa.) and Kynar coated beads can be obtained, for example, from Vertex Image Products (Yukom, Pa.).

The preferred number of beads used with the acoustic dispenser as carriers, assuming a bead with a diameter of 100 microns and a circular membrane with a diameter of about 12.5 cm, can be calculated as follows, the preferred number of beads "n" being in a close pack. $n=\eta D^2/\eta d^2=(D/d)^2=(12.5/100\times10^{-4})$, which is approximately equal to 1.6M. Assuming a density of 4 g/cc, the total mass (m) of the beads is calculated as follows. $m=n\times4/3\eta(d/2)^3\times\rho=1.6\times10^6\times\eta/3(100\times10^{-4})^3\times4$, which is approximately equal to 6.5 grams. Therefore, for 20 grams of bead, there are three layers of beads. Preferably, the amount of beads will be less than or equal to about 3 to about 4 layers.

C. Homogeneity

Preferably, all surfaces that have contact with the objects to be dispensed, such as powder, during normal use of the acoustic dispenser, are all made of the same material, such as polytetrafluoroethylene, so that the charge on the powder will remain the same. Thus, in certain preferred embodiments, the carrier beads used to charge the powder, the container used to hold the powder-bead mixture, and the dielectric coating on the membrane are made of the same material. Alternatively, all surfaces having contact with the objects to be dispensed, during normal use of the acoustic dispenser, are all made of materials having the same triboelectric characteristics.

The present invention is illustrated by the following non-limiting examples.

EXAMPLE 1

Acoustic Dispenser for Particles Less Than About Ten Microns in Diameter

An acoustic dispenser for deposition of particles less than about ten microns in diameter was constructed as follows. A speaker was mounted onto an aluminum plate supported by four pieces of ¾ inch aluminum posts, and an aluminum plate was placed on top of the speaker. A teflon plate was placed on top of the aluminum plate. A membrane made of a 15 mil thick polytetrafluoroethylene ("TEFLON") sheet on a conductive layer was placed on top of the teflon plate. A Corning Pyrex glass cylinder was placed above the membrane and sealed with o-rings. Within the glass cylinder, a mesh was placed above the membrane to separate objects of different sizes, the mesh being a #270 mesh from Newark Wire Cloth Co. (Newark, N.J.). The opening of the glass cylinder permits the placement of a recipient substrate on an electrostatic chuck.

The speaker was activated, and a suspension of 15 g beads and 450 mg powder was used, resulting in the particles of the powder being dispersed in a cloud through the mesh onto the tablet substrate.

EXAMPLE 2

Acoustic Dispenser for Objects More Than About Ten Microns in Diameter

The configuration of an acoustic dispenser for the deposition of objects, such as beads, with a diameter greater than about ten microns was as follows. A Radioshack speaker, catalog number 40-1354A, was placed below an acrylic box with a hinged lid. Inside the acrylic box was a membrane. Suspended above the membrane was an electrostatic chuck for receiving the beads.

The membrane was fabricated using polyimide on copper substrate and a #270 stainless steel mesh from Newark Wire Cloth Co. (Newark, N.J.). Polystyrene beads (Polyscience) with a diameter of 500 μm were used for testing.

The dispenser was activated by applying the beads to the membrane and activating the speaker. The beads were applied to a one mil thick Scotch brand polystyrene tape placed on a metal plate to measure the charge-to-mass ratio of the bead.

Using a bias potential of +1300 V applied to the mesh, 30 nC was collected at a floating plate. 156.6 mg of beads were collected on the floating plate. A q/m (charge to mass ratio) value of 240 nC/g was calculated. At a bias of −1300 V at the mesh, 1 nC was collected and a few beads were collected. These results indicate that the mesh served to positively tribocharge the beads. Further, the use of a teflon layer on top of the mesh may enhance the performance of the acoustic dispenser at −1300 V.

We claim:

1. An apparatus for depositing objects at a deposition site, comprising:
   (a) a vibratory dispenser comprising:
      (i) a vessel with an interior for containing the objects;
      (ii) carriers contained in the vessel for providing a triboelectric charging surface for conferring a triboelectric charge of a first polarity on objects;
      (iii) a membrane for applying a vibration to the carriers and the objects;
      (iv) a source of the vibration, which has an amplitude and frequency effective to propel the carriers; and
   (b) a deposition site, wherein vibrating the membrane causes the objects to become charged through contacts with the carriers and propels at least a population of the objects toward the deposition site.

2. The apparatus of claim 1, wherein the membrane vibrates in the acoustic range.

3. The apparatus of claim 2, comprising:
   (c) an electrostatic chuck for creating one or more electrical fields for adhering a substrate, which electrostatic chuck can be positioned so as to position the substrate at the deposition site so that objects can be deposited on the substrate.

4. The apparatus of claim 2, comprising:
   (d) a sensing electrode for sampling the amount of objects deposited on at the deposition site.

5. The apparatus of claim 2, comprising:
   (e) a charge-mass ratio monitor for sampling the charge-mass ratio of the objects.

6. The apparatus of claim 2, wherein the apparatus is adapted for depositing objects that have an average diameter less than about ten microns.

7. The apparatus of claim 6, wherein the apparatus is adapted for depositing objects that are powder comprising a pharmaceutically active ingredient to manufacture a pharmaceutical.

8. The apparatus of claim 2, wherein the source of acoustic vibration comprises a speaker.

9. The apparatus of claim 2, wherein the source of acoustic vibration comprises a mechanical vibrator.

10. The apparatus of claim 2, wherein the membrane for the application of acoustic vibration comprises (1) a dielectric layer with a first surface facing the vessel interior and an opposing second surface, and (2), facing the second surface, a first conductive layer to which a potential can be applied.

11. The apparatus of claim 10, herein the first conductive layer comprises one or more rings of conductive material to which potential can be applied so that the charged objects are drawn to a center of the membrane.

12. The apparatus of claim 10, wherein the membrane for the application of acoustic vibration further comprises (3), facing the first surface, a second conductive layer having multiple holes which are smaller than the objects applied to the first surface.

13. The apparatus of claim 2, comprising a separating membrane for separating objects from carriers, wherein the separating membrane is positioned between the vessel and the deposition site.

14. The apparatus of claim 2, wherein the carriers are beads and the objects are powder.

15. The apparatus of claim 2, further comprising
   (v) an electrostatic selector mechanism for selecting objects of a first charge polarity, the mechanism comprising:
      a first selector conductor with one or more openings and a second selector conductor within the vessel wherein the two selector conductors are positioned within the vessel such that prior to being dispensed objects flow from between the first and second selector conductors and through the openings in the first selector conductor, wherein voltage can be applied to the first and second selector conductors such that an electrostatic force acts to inhibit objects having a charge of a second polarity from approaching the first conductor.

16. The apparatus of claim 15, wherein the second conductive layer is incorporated in the membrane.

17. The apparatus of claim 15, further comprising:
   (f) a switching mechanism for ending the deposition of objects onto the deposition site, wherein the switching mechanism directs voltage to the first and second conductors such that objects of the first polarity are inhibited from approaching the first conductor.

18. The apparatus of claim 2, wherein every surface of the apparatus having contact with the objects in the interior of the vessel during normal use of the apparatus is made of materials selected to have triboelectric characteristics such that they do not impart to the objects a tribocharge opposite that imparted by the carriers.

19. An apparatus for depositing objects having an average diameter greater than about ten microns at a deposition position, comprising:

(a) a vibratory dispenser comprising:
  (i) a vessel with an interior for containing the objects;
  (ii) carriers for providing a triboelectric charging surface for conferring a triboelectric charge on objects;
  (iii) a membrane for applying a vibration to the carriers and the objects, the membrane comprising a conductive layer having multiple holes, the diameters of the holes being smaller than the average size of the objects, the conductive layer having a first surface facing the interior of the vessel and an opposing second surface;
  (iv) a source of the vibration, which has an amplitude and frequency effective to move the carriers; and
(b) a deposition site, wherein vibrating the membrane causes the objects to become charged through contacts with the carriers and propels at least a population of the objects toward the deposition position.

20. The apparatus of claim 19, wherein the membrane vibrates in the acoustic range.

21. The apparatus of claim 19, wherein the membrane further comprises a second conductive layer and a dielectric layer having two opposing surfaces, one of said dielectric layer surfaces facing the second surface, and the opposing dielectric layer surface facing the second conductive layer.

22. The apparatus of claim 19, wherein the membrane is object impermeable.

23. A method for manufacturing a pharmaceutical by depositing a pharmaceutically active ingredient on a substrate, comprising;
  (a) providing an apparatus comprising a vessel with an interior for holding objects comprising the pharmaceutically active ingredient, which apparatus further comprises (i) a membrane with a membrane surface that is in the interior and (ii) at least one tribocharging surface of a material selected for tribocharging the objects; wherein when the objects have an average diameter of about 50 microns or less the vessel is supplied with carriers for providing tribocharging surfaces, and when the objects have an average diameter of greater than about 50 microns the interior surface of the membrane provides one of the tribocharging surfaces; and
  (b) vibrating the membrane of the apparatus, thereby propelling the objects toward the substrate, wherein the vibration propels the objects so that the objects are triboelectrically charged.

24. The method of claim 23, wherein the objects are particles in a powder.

25. The method of claim 23, wherein the substrate is an edible substrate.

26. The method of claim 23, wherein the vibration is in the acoustic range.

* * * * *